United States Patent [19]

Joseph

[11] Patent Number: 5,656,026
[45] Date of Patent: Aug. 12, 1997

[54] METHOD OF IN VITRO TESTING ONE-WAY PRESSURE GRADIENT LIMITING VALVED GLAUCOMA DRAINAGE IMPLANTS

[76] Inventor: Neil H. Joseph, P.O. Box 332 19 Bayside Ave., East Quogue, N.Y. 11942-0332

[21] Appl. No.: 729,035

[22] Filed: Oct. 9, 1996

Related U.S. Application Data

[60] Provisional application No. 60/005,968 Oct. 27, 1995.
[51] Int. Cl.$^6$ ..................................................... A61M 1/00
[52] U.S. Cl. ................................................................ 604/9
[58] Field of Search ........................... 604/9, 8; 514/913

[56] References Cited

U.S. PATENT DOCUMENTS

| 4,604,087 | 8/1986 | Joseph ..................................... 604/9 |
| 5,433,701 | 7/1995 | Rubinstein ............................... 604/8 |

OTHER PUBLICATIONS

Prata, Jr, et al., In Vitro/In Vivo Flow Char. of Glaucoma Drain. Impl., Dohney Eye Inst. pp. 894–904.

Primary Examiner—Vincent Millin
Assistant Examiner—Robert N. Weiland
Attorney, Agent, or Firm—David A. Tucker

[57] ABSTRACT

A method for in vitro testing glaucoma drainage implants including one-way, pressure gradient limiting valves includes the provision of a fluid environment wherein surface tension effects on the valve are minimal or nonexistant, the location of the valve portion of the implant within the fluid environment, and the application of a gradually varying absolute or average pressure gradient having a small fluctuating pressure superimposed thereon against the valve such that the opening and closing pressures associated with the valve and the presence of any reflux through the valve under pressures below valve closing pressure can be readily and reproducibly determined in vitro.

29 Claims, 2 Drawing Sheets

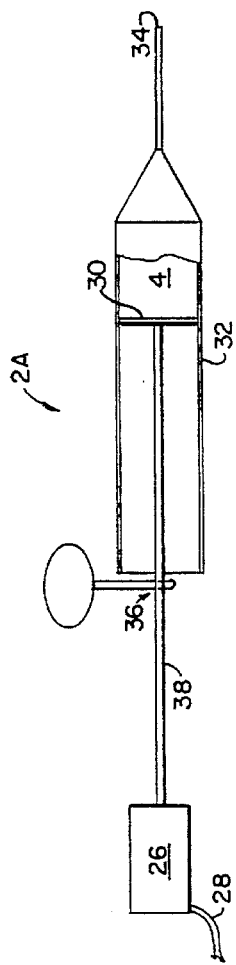
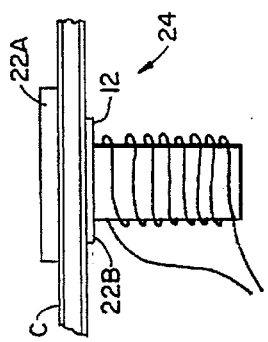
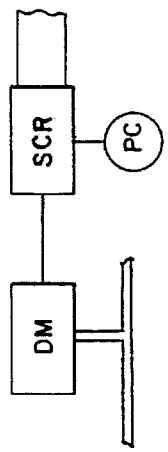
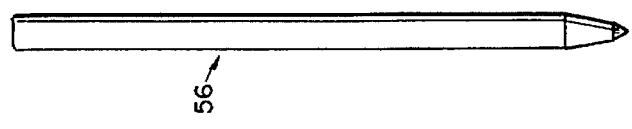

METHOD OF IN VITRO TESTING ONE-WAY PRESSURE GRADIENT LIMITING VALVED GLAUCOMA DRAINAGE IMPLANTS

This application claims the benefit of U.S. provisional application Ser. No. 60/005,968 filed Oct. 27, 1995 by Neil H. Joseph, M.D., for METHOD OF IN VITRO TESTING ONE-WAY PRESSURE GRADIENT LIMITING VALVED GLAUCOMA DRAINAGE IMPLANTS.

BACKGROUND

1. Field of Invention

This invention relates in general to methods of testing surgical implants for the eye. More particularly, the invention relates to methods for the in vitro testing of one-way, pressure gradient limiting valved glaucoma drainage implants prior to the surgical placement of such implants into the tissue of a mammal during the surgical treatment of glaucoma.

2. Summary of the Prior Art

Glaucoma is an eye condition in which, due to various causes, the intra-ocular pressure (that is the pressure of the aqueous humor in the eye) rises. This rise in intra-ocular pressure tends to make the eyeball hard. Further, in high-tension glaucoma, the rise in intra-ocular pressure tends to adversely affect vision, and may cause partial or total loss of sight.

Various methods for surgically treating glaucoma have been developed over the years. Significant among these methods is the surgical implantation of drainage devices which utilize drainage tubes to maintain the integrity of openings formed in diseased eyes for the flow of aqueous humor. In such implant devices, a drainage tube typically provides a passageway designed to extend from the anterior chamber of the eye to a drainage body sutured to the sclera of the eye. The purpose of the drainage body is to increase the available drainage area so as to ensure that aqueous humor drains away from the eye and is absorbed by the body at a sufficiently high, but controlled, rate.

To this end, non-valved aqueous humor drainage implant devices, such as the well knows Schocket Tube or Molteno Glaucoma Drainage Implant, have been utilized. These devices rely upon the back pressure created by a so-called "bleb" of aqueous humor which forms over the drainage body prior to absorption by the body to control the rate of flow of aqueous humor away from the anterior chamber of the eye. These devices, however, have been found to be not totally satisfactory. This is because the flow rate of aqueous humor away from the anterior chamber of the eye is not controlled, at least initially. This tends to result in at least an initial overdrainage of aqueous humor from the anterior chamber of the eye immediately following implantation of the device. Such overdrainage can cause the eye to flatten undesirably, and can also lead to other complications.

For example, a subchoroidal hemorrhage may develop during glaucoma drainage or cataract surgery. As used herein a "subchoroidal hemorrhage" refers to bleeding into a potential space between the choroid (the highly vascular and pigmented layer of tissue adjacent to the retina) and the sclera. Subchoroidal hemorrhages are more serious events than serous, non-bloody, subchoroidal effusions which may represent fluid in and adjacent to swollen choroidal tissue. The latter fluid can resolve itself without scarring or disorganization of adjacent tissue, and without loss of visual acuity or even all vision. Subchoroidal hemorrhages underlying the macula (the area of the retina used for reading quality vision), however, commonly cause some permanent loss of visual acuity and are highly undesirable. This is particularly the case because they are followed by scarring and disorganization of adjacent tissues including adverse changes in light-sensitive cells in the adjacent tissue of the retina, and can result in the loss of all light perception.

To avoid the foregoing problems, numerous implant devices have been developed which include drainage tubes, drainage bodies and means such as one-way pressure gradient limiting valves to control the rate of aqueous humor flow from the eye. Significant among the latter type of devices is the so-called "Joseph device" which is described in detail in U.S. Pat. No. 4,604,087 issued Aug. 5, 1986 to the present inventor. The disclosure of that patent is hereby incorporated by reference into this specification.

In the normal eye of a human being, the pressure of the aqueous humor in the anterior chamber is, on average, typically between about 14 mm and about 16 mm of mercury. Further, it has been determined that a successful glaucoma drainage device is one that ensures that the intra-ocular aqueous humor pressure in the eye remains below 18 mm of mercury for at least six months following its surgical implantation. Hence, the valve opening pressure in the Joseph device is preferably between about 4 mm and about 20 mm of mercury as determined by in vitro testing prior to implantation.

A problem of significance to surgeons, however, remains. This problem relates to the in vitro testing of one-way, pressure gradient limiting valved glaucoma drainage implants prior to their surgical implantation in a patient in association with an eye. Specifically, there is a desire in the art to be able to ensure that a pressure gradient limiting valved glaucoma drainage implant device is both functional and appropriately calibrated prior to its implantation into a patient. Heretofore, a comparison of in vivo and in vitro testing results indicates that current in vitro testing practices do not satisfactorily predict how the device will function in vivo.

The reasons for this are not entirely clear. It is believed, however, that the primary causes of the lack of correspondence of in vitro and in vivo testing of pressure gradient limiting valved glaucoma drainage devices resides in the facts that (1) current in vitro ophthalmic testing methods are not dynamic, and (2) current ophthalmic testers have failed to fully comprehend the environmental, material and geometrical factors inherent in the devices tested and the test procedures adopted.

The eye normally has pressure fluctuatingly applied to it by the effects of heartbeat (pulse), breathing, crying, temperature, level of motor activity, variations in aqueous humor secretion over time, and changes in posture or bodily orientation, among others. Further, the in vivo environment consists of wet tissue. Nevertheless, current ophthalmic testing procedures are typically conducted in a gaseous environment (i.e., air), and apply only a gradually varying absolute pressure gradient to the valve of the device.

It has been found that such testing can result in differences in measurements of the opening pressure of the valve of the device being tested taken within an hour of each other which exceed 10–20 mm Hg. This is an unacceptable repeatability of results. In fact, the Apr. 20, 1996 work group meeting of the American National Standards Institute Z-80 Committee on Glaucoma Drainage Implants has gone so far as to indicate that "Non-physiologic flow rate studies and studies done in air do not contribute useful information to the user (of one-way pressure gradient limiting valved glaucoma drainage implants)" (parenthetical added).

Accordingly, it will be understood that current ophthalmic testing does not approximate the environment into which the implant is to be placed for operation. It also will be understood that due to the viscosity and elasticity of silicone rubber and the presence of van der Waals forces between the clean, smoothly cut opposed surfaces of slit valves formed therein, the slit valve flaps tend to stick together unless subjected to physiologic flow of aqueous humor or cerebrospinal fluid, constantly irrigated or otherwise treated. Further, it will be understood that testing in air creates an air/liquid interface at the slit valve exit. This interface introduces a surface tension effect which must be overcome in opening the slit valve thereby unacceptably detracting from the meaningfulness of the test results generated.

Testing in a liquid environment (i.e., with the slit valve located in a water bath) has been conducted previously. This reduces or eliminates the surface tension effect when water is used as the fluid applied to the valve under pressure to determine its opening characteristics. It, however, does not fully deal with this problem when other substances more closely allied with the composition of aqueous humor are utilized as the pressure applying liquid.

Studies of hydrocephalus shunt valves and heart valves have heretofore noted the importance of pulsate flow, temperature and time-in-service on valve performance. However, whatever potential relevance these studies may have in the very specialized ophthalmic context either has gone unrecognized in the art, or has been discounted because hydrocephalus shunt valves are required to function at much higher flow rates and with much higher pressure fluctuations than are expected in eyes.

SUMMARY OF THE INVENTION

Accordingly, it is an object of the present invention to provide a method of testing one-way, pressure gradient limiting valved glaucoma drainage implants resulting in measurements of valve opening and closing pressures which are at least substantially unaffected by surface tension effects.

It is also an object of the present invention to provide a method of testing one-way, pressure gradient limiting valved glaucoma drainage implants resulting in measurements of valve opening and closing pressures having improved repeatability.

Another object of the present invention is to provide a method for testing one-way, pressure gradient limiting valved glaucoma drainage implants resulting in measurements of valve opening and closing pressures shortly after the valve is formed so as to simplify manufacturing procedures and reduce manufacturing costs.

Yet another object of the present invention is to provide a method for testing one-way, pressure gradient limiting valved glaucoma drainage implants resulting in measurements of valve opening and closing pressures a substantial period of time following the manufacture of such implants so as to thereby detect changes in valve properties over time.

A further object of the present invention is to provide a method for repeatedly testing one-way, pressure gradient limiting valved glaucoma drainage implants resulting in measurements of valve opening and closing pressures over extended periods of time after the valve is formed so as to detect changes in valve properties over time as an accelerated fatigue test.

Still a further object of the present invention is to provide a method for testing one-way, pressure gradient limiting valved glaucoma drainage implants resulting in repeated measurements of valve opening and closing pressures so as to evaluate existing devices prior to their surgical implantation, and/or to evaluate new materials and designs.

Still another object of the present invention is to provide a method for testing one-way, pressure gradient limiting valved glaucoma drainage implants resulting in measurements of valve opening and closing pressures with readily available, inexpensive and non-motorized equipment.

Another object of the present invention is to provide a method for testing one-way, pressure gradient limiting valved glaucoma drainage implants resulting in measurements of valve opening and closing pressures which enable surgeons to verify valve performance prior to device implantation or to determine valve performance for scientific study or demonstration.

Another object of the present invention is to provide a method for testing one-way, pressure gradient limiting valved glaucoma drainage implants resulting in measurements of valve flow rates under dynamic conditions of fluctuating pressure at varying absolute pressure levels.

Another object of the present invention is to provide a method for testing one-way, pressure gradient limiting valved glaucoma drainage implants which results in measurements of valve opening pressures as a function of steady flow rates of liquid under fluctuating pressure conditions.

Another object of the present invention is to provide a method for testing one-way, pressure gradient limiting valved glaucoma drainage implants resulting in measurements of valve opening and closing pressures under conditions approximating the environment into which the implant is to be surgically placed.

Another object of the present invention is to provide a method for testing one-way, pressure gradient limiting valved glaucoma drainage implants including steps calculated to remove the effects of extraneous physical, geometrical or material limitations of the device from the measured valve opening and closing pressures.

These, and other, features, objects and advantages of the invention are achieved by a method generally comprising in a preferred embodiment the following steps:

1. providing:
   a) a one-way, pressure gradient limiting valved glaucoma drainage implant to be tested, the implant having a free drainage tube end;
   b) source means for providing a flow of test liquid;
   c) first pressure application means for applying an absolute pressure gradient across the valve being tested;
   d) means for measuring the absolute pressure gradient applied to the valve;
   e) second pressure application means for superimposing a fluctuation on the applied absolute pressure gradient;
   f) recording means for recording valve opening and valve closing pressures;
   g) illumination means for lighting the valve output;
   h) first flow detection means for determining the presence and/or absence of flow from the valve output;
   i) a fluid environment wherein surface tension artifacts at the valve exit are minimized;
   j) support means in the fluid environment for holding the valve portion of the implant;
   k) second flow detection means for determining the quantity of flow through the valve output;
   l) connection means for conveying test liquid from the source to the free end of the drainage tube of the implant;

m) timing means for determining elapsed test time;
n) heat control means for controlling the ambient temperature of the test site; and
o) means for manipulating the valve being tested;

2) Inspecting the one-way, pressure gradient limiting valved glaucoma drainage implant for defects;

3) Manipulating the valve to be tested with the manipulating means;

4) Mounting the valved portion of the implant on the support means in the fluid environment;

5) Connecting the free end of the drainage tube of the implant to the source via the connecting means;

6) Applying the testing liquid to the valve under the influence of the first and second pressure application means;

7) Gradually increasing the absolute pressure until test liquid flow through the valve is detected by the first fluid flow detection means;

8) Recording the absolute pressure at which liquid flow through the valve was detected;

9) Gradually reducing the absolute pressure until test fluid no longer is detected by the first fluid detection means;

10) Recording the absolute pressure at which liquid flow through the valve ceased;

11) Recording the quantity of test fluid which passed through the valve between steps 7 and 10 as determined by the second flow detection means; and 12) Reducing the absolute pressure to a level about 20 mmHg below the pressure at which liquid flow through the valve ceased to ensure the absence of backflow (i.e., reflux) through the valve.

It, therefore, will be recognized that the present invention proceeds from the realization that the problems with current methods for in vitro testing of pressure gradient limiting one-way valved glaucoma drainage implants made of flexible, biologically inert materials such as silicone rubber do not reside solely in the fact that such devices are conventionally tested by variations in absolute applied pressure to the valve in a gaseous environment (i.e., air). Rather, these problems arise primarily by virtue of surface tension artifacts at the valve exit and a failure of prior art methods to utilize dynamic pressure generation means in the application of test pressures to the valve under consideration.

To overcome this problem, the present invention contemplates that in a representative preferred embodiment, a reservoir such as an open topped, vertically oriented syringe barrel is provided. The syringe barrel may be vertically raised and/or lowered with a deliberately, horizontally oscillating hand or equivalent mechanically powered device.

A vertically oriented centimeter ruler (marked at 1.36 cm intervals) is located substantially immediately adjacent and parallel to the vertical travel path of the syringe barrel.

The lower end of the syringe barrel is attached to one end of a blunt, 26 gauge, first cannula. The other end of the first cannula is connected to (i.e., telescopically fit into) one end of a polyethylene tube having an internal diameter of a little less than 0.5 mm. The other end of the polyethylene tube is connected to (i.e., telescopically fit around) one end of a second 26 gauge cannula. The other end of the second cannula is connected to (i.e., telescopically fit into) the free end of the drainage tube of the one-way, pressure gradient limiting valved glaucoma drainage device to be tested.

The valved glaucoma drainage device may be conveniently attached to a portion of the form utilized to form its large explant, and be positioned on the stage of a dissecting microscope. The magnification range of the dissecting microscope is typically between about 6 and about 150 diameters, and is operable with focal, as well as direct and ambient, light illumination. The valved glaucoma drainage device also is preferably positioned in a bowl or similar container in a fluid environment.

In this embodiment of the invention, the syringe barrel, the polyethylene tube, the first and second cannulas, the drainage tube of the valved glaucoma drainage device and the bowl are all filled with essentially the same liquid—in this case water or normal saline solution. The liquid in the reservoir is rendered visible, in contrast to the transparent and colorless liquid in the bowl or container by adding to the reservoir a watery liquid containing a dye or pigment. This dye or pigment may comprise for example a few drops of India ink, or a dilute methylene blue dye, or a sodium fluorescein solution.

The portion of the form utilized to mold the large explant of the valved glaucoma drainage device is stabilized in the bowl or container by a rack to prevent its rolling or sliding therein. This is necessary since rolling or sliding of the valved glaucoma drainage device would impair the exacting microscopic observation of the initiation and/or cessation of liquid flow through the valve.

In addition, the bowl or container may be provided with a clear liquid inflow and an exit spillway. This eases the viewing of the initiation and/or cessation of the flow through the valve of the device being tested and any reflux back through the valve.

With this set up the method proceeds as set forth in steps 2 through 10 above. Specifically, after the valve has been manipulated to ensure that it has not been sealed together either by van der Waals forces or otherwise, the syringe barrel is moved vertically upwardly and at the same time reciprocated horizontally until liquid flow through the valve is viewed through the microscope. The upward vertical movement of the syringe barrel imparts an increase in absolute pressure to the colored liquid and the horizontal motion superimposes a fluctuation on the gradually increasing applied absolute pressure. This mode of motion imparts an increasing pressure to the fluid pressing against the valve in the fluid environment of the bowl or container so as to more closely approximate the conditions the valve will encounter in use after its implantation in the body of the patient.

The valve opening pressure is then determined by reading the level of the upper surface of the fluid in the syringe barrel on the adjacent vertical ruler. This reading is readily convertable to a pressure measurement in the manner discussed in further detail hereinbelow.

Thereafter, the syringe barrel is gradually lowered vertically—again while reciprocating the syringe barrel horizontally—until the flow of colored liquid through the valve ceases. The level of the upper surface of the fluid in the syringe barrel again is read on the vertical ruler, and that reading is converted to a pressure measurement.

As indicated above, the quantity of liquid passing through the valve during the period between valve opening and valve closing may also be measured with the above-described test apparatus. Specifically, the bowl or container spillway may be oriented relative to the starting level of liquid therein such that any additional liquid entering the bowl or container will cause a corresponding quantity of liquid to leave the container through the spillway.

By measuring the quantity of liquid so discharged from the bowl or container during a preselected time period, one may approximate the flow rate through the valve between its opening and closing. Of course, other means for the measuring of the flow of liquid through the valve may be used without departure from the present invention in its broadest aspects.

The significant point is that the quantity of liquid flow through the valve between its opening and closing under the above test conditions may be very important to the calibration of the one-way, pressure gradient limiting valved glaucoma implant. This is because overdrainage of the anterior chamber of the eye can cause serious problems which may require additional surgery to correct—if indeed those problems and/or complications are correctable at all.

Finally, the syringe barrel is lowered below the level at which liquid flow outwardly through the valve ceased. This motion of the syringe barrel results in the application of a fluctuating pressure to the valve which is negative with respect to the closing pressure of the valve in a manner similar to that expected to result from the fluctuating forces applied to the eye discussed above.

Accordingly, the test method of this invention provides significant information regarding the flow of liquid through the valve in both directions. This is deemed to be important because the purpose of the implant is to remove excess aqueous humor from the eye in a controlled manner. The valve, therefore, should open and close in response to the pressure in the anterior chamber of the eye, and should not inject previously drained liquid back into the anterior chamber of the eye in response to fluctuating pressures applied to the so-called "bleb" of unabsorbed aqueous humor at the drainage explant.

In another embodiment, testing is done in a gaseous environment with the valve being treated with an appropriate surfactant preparation. The surfactant resolves the surface tension problem such that meaningful results may be obtained by testing under dynamic applied pressures in either a gaseous environment or in a liquid environment wherein the bath is composed of material(s) significantly different from the test liquid flowing through the valve.

BRIEF DESCRIPTION OF THE DRAWINGS

A more complete understanding of the present invention will be attained by those skilled in the art from the following detailed description of a preferred embodiment thereof in conjunction with the attached drawings in which:

FIG. 2 is an illustrative, cross-sectional, elevational view of a 1 ml, narrow, "tuberculin" syringe having a blunt, 0.5 mm external diameter, hypodermic cannula attached to its output end suitable for use in manipulating a glaucoma drainage implant valve;

FIG. 3 is an illustrative elevational view of a disposable razor-blade fragment knife suitable for use in forming a slit valve in a silicone drainage tube of a glaucoma drainage implant;

FIG. 4 is an illustrative, cross-sectional side elevational view of a variable motor driven syringe capable of supplying a flow of liquid at various preselected constant flow rates to the valve of the glaucoma drainage implant being tested;

FIG. 5 is an illustrative side elevational view of a variable electromagnetically controlled device adapted to alternatingly narrow and widen the lumen of a length of elastic tubing extending between its contacts so as to superimpose an oscillation onto the pressure of a liquid flowing through the tubing;

FIG. 6 is an illustrative depiction of a light source L and a photodetector PC located on opposite sides of a valve to be tested such that the onset and cessation of liquid flow through the valve may be detected therewith; and FIG. 7 is an illustrative depiction of a digital manometer connected to the pathway of test fluid between the source thereof and an implant being tested, a photodetector adapted to detect the passage of fluid through the test liquid pathway, and a strip chart recorder connected to both the digital manometer and the photodetector for recording output signals therefrom.

DETAILED DESCRIPTION OF PREFERRED EMBODIMENT

Figure 1:
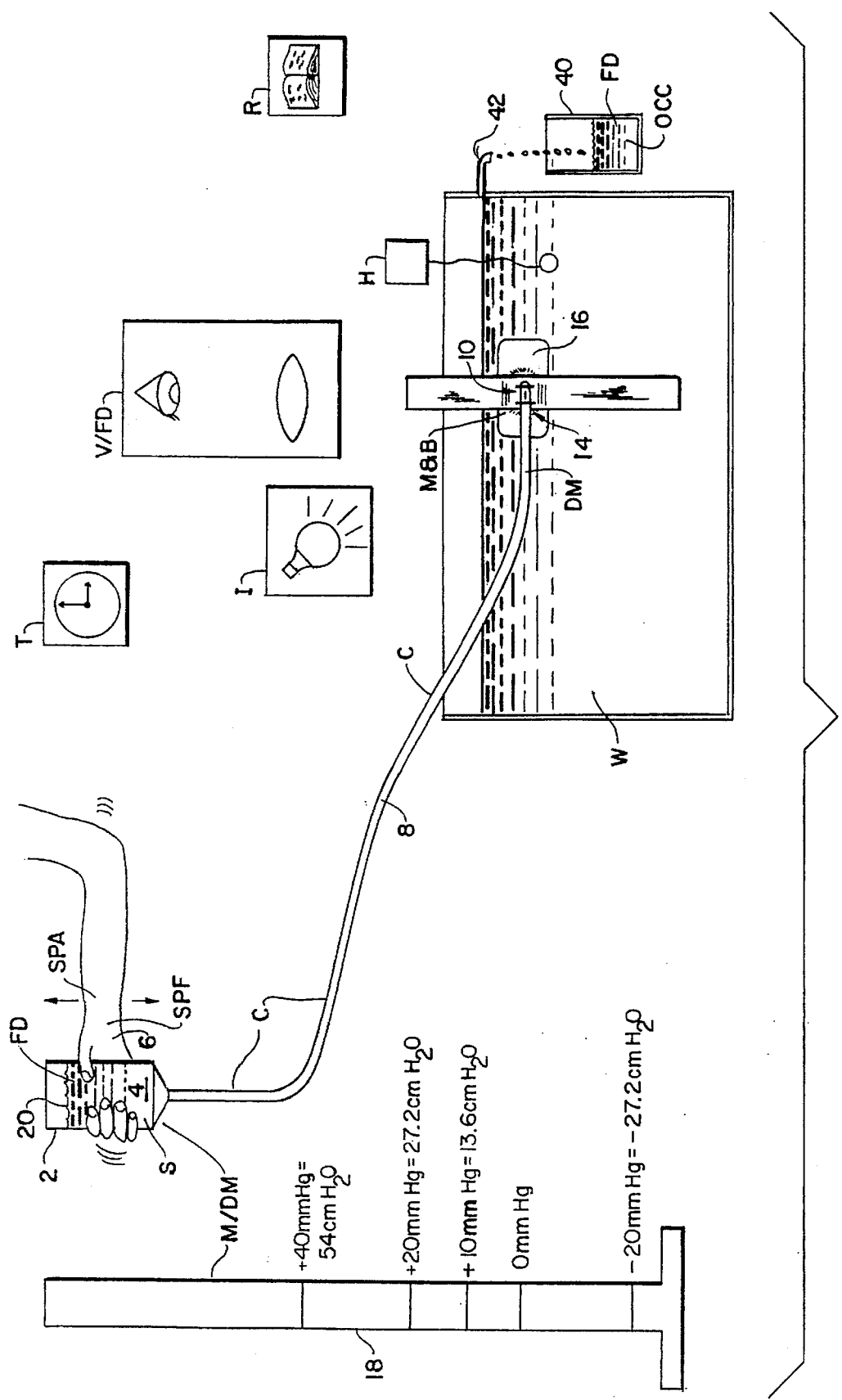
FIG. 1 is an illustrative depiction of one preferred test set up for use in the practice of the method of the present invention.

Referring now to the drawings, and particularly to FIG. 1, a simple apparatus suitable for use in the testing of one-way, pressure gradient limiting valved glaucoma drainage implants, such as that disclosed in U.S. Pat. No. 4,604,087 mentioned above, under dynamic flow conditions is shown. As used herein, the term "dynamic flow conditions" means conditions under which the pressure applied by the test liquid which moves through the implant and out of the valve is altered by both (i) repeatedly changing the absolute applied pressure, and (ii) by the superimposition of fluctuations onto the absolute applied pressure.

In the embodiment shown in FIG. 1, dynamic flow conditions are achieved by moving the source of test liquid S (depicted as an open topped, vertically oriented syringe barrel 2 filled with test fluid 4 and held in a hand 6, or some other source of absolute applied pressure SPA or superimposed fluctuating pressure SPF) up and down vertically while simultaneously gently shaking the syringe barrel 2 (or some other portion of the test fluid pathway 8 to the device 10 being tested) substantially horizontally (i.e., generally perpendicular to its longitudinal axis) on the order of about twice per second. The maximum vertical travel of syringe barrel 2 is contemplated to be on the order of between about 50–60 cm above and about 15–30 cm below the level of the one-way, pressure gradient limiting valve of the glaucoma drainage implant 10 being tested.

The horizontal travel of the syringe barrel 2 measured relative to its vertical axis, on the other hand, is contemplated to be on the order of between about 0.0001 cm and about 15 cm right or left, and preferably on the order of about 2 mm right or left. Further, it is to be understood that the amplitude, waveform and frequency of the horizontal shaking need not be perfectly regular in order to achieve the results contemplated by this invention.

For example, the oscillatory movement of the syringe barrel 2 might be accomplished by tapping the syringe barrel approximately twice per second with the tip of a finger such as the index finger of the hand 6 which holds the syringe barrel 2. Alternatively, the horizontal movement of the syringe barrel 2 (reservoir) might be induced by attaching or coupling the syringe barrel 2 to an alternative vibration source SPF such as a variable speed electrical air pump, a motorized vibrator, a contact of an electrical device or some other comparable means well known in the art in any convenient manner and with or without a layer of cushioning material 12 (see FIG. 5) therebetween.

Similarly, the oscillatory movement of the syringe barrel 2 may be set at a convenient frequency, such as between about 50 and about 60 cycles per second. Alternatively, however, physiologically significant frequencies such as about 72 per second (roughly consistent with a human heart rate) or about 12 cycles per minute (comparable to a normal human breathing rate) might be selected.

It has been found that each of the above oscillatory frequencies applied to the syringe barrel (reservoir) provides certain relevant information when used in the test method of this invention. In practice, however, the best results have been achieved with a variable speed oscillator attached, or coupled to, the syringe barrel 2. More particularly, the most significant test results are those wherein the initiation and the cessation of flow through a one-way valve recently flushed through with a watery liquid repeatedly and promptly occurs within a relatively narrow range of measured absolute pressure gradient measurements, such as about 1 mm Hg or 2 cm of applied water pressure against the valve.

Hence, it will be understood that the frequency and intensity of the oscillatory motion imparted to the syringe is preferably variable. This allows the tester to correlate the applied absolute pressure and the applied dynamic pressure so as to approximate the physiologic environment into which the implant is to be placed for use in the human body. Accordingly, the tester is provided with at least some repeatable results which are indicative of the practical utility of the implant for in vivo usage.

The syringe barrel 2 is connected to the one-way, pressure gradient limiting valved glaucoma implant 10 by connecting means C. In one possible form of the embodiment shown in FIG. 1, connection means C comprises a first and a second 26 gauge, blunt, hypodermic cannula having an external diameter of 0.5 mm, and a length of flexible polyethylene tubing having an internal diameter of slightly less than 0.5 mm.

The first cannula is attached at one end to the outlet of the syringe barrel, and its other end is press fit into one end of the length of polyethylene tubing. One end of the second cannula is press fit into the other end of the length of polyethylene tubing while the other end of the second cannula is telescoped into the open end of the drainage tube of the implant, here a 0.30 mm internal diameter Silastic tube.

The implant is placed on a support means M&B suitable for the particular implant to be tested. In the embodiment shown, the support means comprises a portion 14 of the mold on which the implant was formed and a block 16 adapted to support that mold portion. The mold portion and the block together act to hold the implant in a stable position in a controlled fluid environment, here slightly below the surface of a water bath W, for microscopic observation of the valve of the implant (see V/FD).

For practical clinical purposes, it has been found to be satisfactory to test one-way, pressure gradient limiting valved implants, such as the Joseph device described in U.S. Pat. No. 4,604,087, at room temperature of approximately 25° Centigrade. Accordingly, the heat control means H for the controlled fluid environment (i.e., water bath W) may be the thermostatically controlled heating system of a centrally heated and air-conditioned building. Of course, the temperature of the test environment could be directly controlled by separate heating and/or cooling devices, if desired.

In the test apparatus shown in FIG. 1, the pressure gradient applied across the valve of the implant is proportional to the vertical distance between the valve just below the surface of water bath W and the upper surface 20 of the test fluid 4 in syringe barrel 2. It has been found to be convenient to measure this distance in increments of 1.36 cm because such increments correspond to 1 mm Hg in a gravity feed system such as that shown. Accordingly, a vertical ruler 18 marked in 1.36 cm increments is provided parallel and adjacent to the vertical travel path of the syringe barrel 2. This allows the syringe barrel and the ruler to together function as a manometer M/DM for measuring the applied pressure gradient across the valve. This manometer may be read directly by observation, or a digital manometer connected to a strip recorder or other data recording means for tracking the course of each test may be utilized (See FIG. 7).

The means for applying average or absolute gradient pressure SPA across the valve in this particular embodiment is the gradual manual vertical movement of the syringe barrel 2. It, of course, will be recognized that the vertical movement of the syringe barrel 2 also might be accomplished with a rack and pinion gear arrangement, a belt or chain or wire or rope attached at one of its ends to the reservoir and extending over a pulley, hydraulic or pneumatic lifts, a constant or variable speed electric motor, a clockwork motor, a wheel turned either by hand or mechanically, or some other device without departure from the present invention in its broadest aspects.

Assuming that a level of the valve just below the surface of the liquid in the water bath W corresponds to 0 mmHg, the above-described vertical movement may conveniently be between a location in which the upper meniscus 20 of the test fluid 4 in the syringe barrel 2 is 27.2 cm below the level of the valve (i.e., at −20 mmHg) and a location at which the upper meniscus of the test fluid in the syringe is 54.4 cm above the level of the valve (i.e., at +40 mm Hg).

The means for providing a superimposed fluctuation in the absolute or average gradient pressure across the valve in this embodiment is the gentle horizontal manual shaking of syringe barrel 2. This gentle horizontal shaking causes ripples to form on the surface 20 of the test liquid 4 in syringe barrel 2. These ripples signify that the applied pressure gradient to the valve fluctuates slightly above and below the steady state absolute or average pressure gradient across the valve caused by the vertical movement of syringe barrel 2. These fluctuations (in the ideal case) approximate the true conditions encountered by the valve after implantation. Their presence has been found to result in more repeatable and consistent valve opening and valve closing pressure measurements to be observed than in test methods which rely solely on variations in absolute or average pressure gradients.

The superimposed fluctuation upon the absolute or average pressure gradients also could be achieved by applying a vibration to the elastic walled tubing which connects the test liquid source S to the open end of the drainage tube of the implant 10 being tested. Also, a similar result could be achieved by alternately narrowing or restricting, and widening the lumen of the connecting means C.

As shown in FIG. 5, one way to accomplish this would be to place a portion of the connecting means C (i.e., a length of elastic tubing formed of polyethylene, silicone rubber, Tygon or other elastic material) between the contacts 22A and 22B of an electrical device 24. By supplying alternating current to device 24, its contacts will be caused to alternately exert a compressive force, and not exert a compressive force, on the elastic tubing carrying the test liquid.

The elastic nature of the tubing allows the narrowing of the lumen of the tubing in response to the application of an electromagnetically derived compressive force applied by the contacts against the tubing wall and the cushioning material 12 as shown in FIG. 5. The elastic recoil of the tubing and the perfusion pressure of the test liquid flowing therethrough causes a widening of the lumen back toward its original round, extruded, cross-sectional shape during the intervals when the compressive force of the contacts is not present. Hence, the periodic application of the electromagnetically derived compressive force to the contacts of the device 24 superimposes a fluctuating pressure onto the absolute pressure of the test fluid being conveyed from the source 2 to the implant 10 being tested. However, in the latter regard, care must be taken not to totally occlude the tubing. This is because the periodic total occlusion of the tube lumen would effectively create a second valve between the source and the pressure gradient limiting valve being tested. Obviously, the presence of such a valve would effectively destroy the ability of the method of this invention to provide meaningful results concerning the pressure gradient limiting valve under consideration.

Further, a constant flow rate of the test fluid to the implant being tested may be assured by the use of a constant speed syringe pump device 2A such as that illustratively shown in FIG. 4. Such a pump, or a manually operated alternative 2B as shown in FIG. 2, may also be used to "flush through" the implant (i.e., manipulate the flaps of the valve being tested) prior to the application of physiologically relevant test pressure to the implant valve.

Specifically, in the exemplary motorized, constant speed syringe pump 2A shown in FIG. 4, the syringe pump 1 includes a variable speed electrical motor 26 connected to a power source (not shown) by cord 28. Motor 26 drives a plunger 30 in syringe barrel 32 so as to force test fluid 4 in the syringe through its narrow outlet 34 in a controlled manner. Further, in the embodiment shown a keyway 36 engaging a longitudinal side slot (not shown) in the plunger driver 38 prevents rotational movement of the plunger in the syringe barrel and also may restrict the longitudinal travel of plunger 30 in syringe barrel 32.

The illumination means I may comprise various light sources such as windows, artificial diffuse room illumination devices, or focal illumination means associated with the microscope stage (see V/FD). White light is deemed to be sufficient if a methylene blue dye solution or India ink pigment suspension is used to facilitate the observation of test liquid in the area of the valve in contrast to the clear, purer, liquid such as water in the water bath W.

However, if one elects to use the fluorescent dye fluorescein to tint the test liquid relative to the clear liquid in the water bath W, it has been found to be beneficial to include a cobalt blue filter in one of the light paths from a light source to the valve area. This filtered light causes the dye to emit a yellow/green light which shows up under microscopic observation at very low concentrations. Therefore, it greatly assists an observer in accurately determining the onset of valve opening and the completion of valve closing. It also is very useful in determining whether or not reflux (i.e., backflow) occurs in a particular valve after valve closure has been determined.

The timekeeping means T in the present embodiment comprises a wristwatch or wall clock in any conveniently visible location. It will be understood, however, that depending upon the sophistication and/or automation of devices utilized in place of the other elements of the test apparatus, the timekeeping means T may be made more accurate and may be directly coupled with others of the elements of the apparatus within the skill of one in this art.

Similarly, the recording means R of the present embodiment is comprised of a laboratory notebook and a pencil or pen. Obviously, however, more sophisticated recording means such a strip recorders SCR (see FIG. 7) or other automated devices could be used without departure from the present invention in its broadest aspects.

The first and second flow detection means FD and V/FD might comprise the following elements in the preferred embodiment shown in FIG. 1. Means such as a pan 40 may be provided for collecting an outflow OCC from the water bath W equal in volume to the flow of test liquid through the valve. In this case, the level of liquid in the water bath lies just below a spillway 42. When test liquid 4 flows through the valve of the implant, an equivalent volume of liquid flows out of the water bath W into the pan 40. This volume can be measured and correlated with elapsed time of valve opening to yield a flow rate.

It, of course, will be understood that the flow detection means in an automated set up within the broadest aspects of this invention might include a light source L (46) and a photodetector PC (44) as illustratively shown in FIG. 6. In such a case, the light source L (46) of nearly parallel, or of parallel, light rays would be located on one side 54 of the valve 50 being tested, and oriented so as to cast its narrow beam 52 across the outer edge of the valve in the direction indicated by arrows 45. The photodetector PC (44), on the other hand, would be disposed on the other side 48 of the valve being tested, and oriented so as to normally receive the light beam 52 from light source L (46). Hence, the interruption of light beam 52 by droplets and/or a flow of test fluid through the valve (see FIG. 1) would be detected by the photodetector PC (44). Cessation of test fluid flow through the valve in such a test set up also would be detected by the photodetector's recognition of the resumption of its receipt of the light beam 52 from the light source L (46). Further, other forms of motion detectors also might be used depending upon the particular nature and components of the test set up utilized.

Similarly, the level 20 of test liquid 4 in syringe barrel 2 can be viewed visually so as to yield a volume indication which when combined with an elapsed time measurement of valve opening results in a flow rate through the valve. Still further, flow detection through the valve in the present embodiment also may be accomplished by visual observation of the valve through the microscope V/FD.

As alluded to above, the presence of a dye in the test fluid facilitates this observation. Specifically, the observer can determine valve opening, fluid flow, valve closing. Further, even in the case of badly defective one-way valves, the backward flow at modest reduced pressure gradients of about 20 mm Hg below the closing pressure of the valve may be detected by the location and movement of colored liquid relative to the valve.

Again it must be understood that more sophisticated equipment may be utilized without departure from the present invention. Hence, just as the pressure application means is not limited to vertically moved and shaken gravity feed means as described above, the fluid detection and/or liquid flow means may be any one, or a combination of, more sophisticated devices without departure from the present invention in its broadest aspects.

More particularly, the liquid flow detector might be any one of a number of fluid flow detection devices (see generally element DM in FIG. 7). Such devices might include, for example, flowmeters driven by elements in the flow or acting through electrical or analog transducers to produce a reading of the presence and/or volume of liquid flow.

Similarly, the pressure application means might also comprise an electrically driven roller pump using elastic tubing such as silicone rubber tubing and a roller to propel segments of liquid around a partial circle; diaphragm pumps; an electrically driven syringe; or even a bag of liquid which is squeezed by the application of air or gas pressure applied to an inflatable rubber bladder.

The desired fluctuations on the absolute or average pressure further might be produced by slapping an elastic tube through which the liquid is flowing with a hard object such as a ruler to compress the tubing against a firm surface. Similarly, alternating current may be used to compress the tubing between an electromagnet and a piece of carbon steel as representatively illustrated in, a described above with regard to, FIG. 5. Further, a modified Brewer automatic pipetting machine could be used, as could a commercially available pulsation unit which incorporates a diaphragm pump mechanism.

As shown in FIGS. 2 and 3, the test apparatus may comprises a narrow-barreled, water-filled 1 ml so-called "tuberculin" syringe (valve manipulation means) 2B having a blunt, 26 gauge (i.e., external diameter 0.5 mm) steel cannula attached to its outlet port, and a razor blade fragment knife 56 (see FIG. 3). The 1 ml syringe 2B may be used to inject 1 ml of water or other test liquid rapidly into the free end of the drainage tube of the implant. The liquid so injected forces the flaps of the valve open and is ejected from the valve as a liquid jet at a right angle to the tube over the explant portion of the implant device.

It will be understood, therefore, that the injected liquid separates and wets the valve leaflets (flaps) so as to assure that repeatable testing of the valve may be performed at physiologically significant valve opening pressures during time periods of up to one hour or more after such valve "flush through". It will also be understood that physical manipulation of the valve leaflets may be required prior to such "flush through" in order to overcome van der Waals forces therebetween and/or to remove contaminants or excess glue which may tend to hold the valve closed after initial manufacture or sterilization procedures utilizing salt solutions.

If the implant has not had its valve formed prior to the initiation of the test procedure, or if the opening pressure exceeds 20 mm Hg in a Joseph implant after several test cycles, the valve may be cut for the first time or extended to about 4 mm in a Joseph device with the razor blade fragment knife 56 (see FIG. 3). To date it has been found that the opening pressure of the valve should not exceed about 20 mm Hg and that, at least in the Joseph version of the implant, the length of the slit valve should not exceed about 4 mm. Accordingly, in one-way, pressure gradient limiting valved glaucoma drainage implants utilizing a slit valve in the drainage tube, the length of the longitudinal slit in the drainage tube should not exceed about 4 mm and the pressure required to open that valve should not exceed about 20 mm Hg. If measurements of these parameters during the test procedure exceed these values, the device is destroyed as being unsatisfactory under the present protocols of the present method.

The apparatus just described is used to test one-way, pressure gradient limiting valved glaucoma implants for their suitability for implantation into patients based upon any relevant regulatory requirements and/or test measurement limit protocols established by the individual tester and/or surgeon involved. This test method proceeds by the performance of the following steps. It will be understood by those skilled in the art that the following steps 5–9 should be repeatable and reproducible (i.e., done at least two (2) or more times with closely similar results each time).

1) Inspecting the one-way, pressure gradient limiting valved glaucoma drainage implant for defects;

2) Manipulating the valve to be tested with the manipulating means;

3) Mounting the valved portion of the implant on the support means in a fluid environment;

4) Connecting the free end of the drainage tube of the implant to the source via the connecting means;

5) Applying the testing liquid to the valve under the influence of first and second pressure application means (which respectively apply an absolute pressure and a fluctuation superimposed thereon);

6) Gradually increasing the absolute pressure until a test liquid flow through the valve is detected by a first fluid flow detection means;

7) Recording the absolute pressure at which liquid flow through the valve was detected;

8) Gradually reducing the absolute pressure until test fluid no longer is detected by the first fluid detection means;

9) Recording the absolute pressure at which liquid flow through the valve ceased;

10) Recording the quantity of test fluid which passed through the valve between steps 7 and 10 as determined by a second flow detection means; and 11) Reducing the absolute pressure to a level about 20 mmHg below the pressure at which liquid flow through the valve ceased in order to ensure the absence of backflow (i.e., reflux) through the valve.

More particularly, in the preferred test method and quality control sequence, the method begins with a visual inspection of the implant to be tested, which for the sake of convenience will hereinafter be assumed to be a Joseph implant as described in U.S. Pat. No. 4,604,087. It should be understood, however, that it is contemplated that the method in its broadest aspects applies equally to substantially any presently known one-way, pressure gradient limiting valved glaucoma drainage implant, or to designs not yet constructed.

The medical grade, silicone rubber implant, while still on a portion of the mold on which it was formed and with the drainage tube curved and having its distal end attached to the explant with, and blocked by, medical grade silicone rubber adhesive is visually inspected for particle contamination and satisfactory shape and thickness. This inspection is achieved first with the naked eye of the the tester, and thereafter under a dissecting microscope. At this time, any undesirable excess bulk of medical grade silicone rubber adhesive may be trimmed away. Such trimming is customarily achieved under the microscope with a cutting instrument representatively shown in the drawings (FIG. 3) as a razor blade fragment knife, although other cutting instruments such as a small pair of scissors or a razor blade might also be used.

The method proceeds next with the the attachment of the implant to be tested to the connection means C. As mentioned previously, this is accomplished by inserting the free end of the second cannula of the connecting means into the open, free, inflow end of the drainage tube of the implant. This creates a continuous flow path for test liquid between the open topped syringe barrel 2 and the valve site. Accordingly, test liquid may flow from source S to the valve site under the force of gravity, or flow from the valve site toward source S in the event that the closure of the valve is not perfect or the valve is not perfectly one-way in its operation under conditions of reverse applied pressure.

The syringe barrel 2 is filled with a watery liquid without air bubbles. The watery liquid may be water, normal saline solution, or any other watery test liquid of interest such as a liquid having viscosity and other characteristics approximating the characteristics of the aqueous humor normally secreted within the eye with which the implant is to be used. Conveniently, a small quantity of a dye such as methylene blue or fluorescein, or a pigment suspension, such as India ink, may be added to the contents of the source S. This renders the test liquid perfusing the implant readily visible and distinguishable from the otherwise identical liquid content of the water bath W previously described.

In the case wherein the test apparatus is used both to test the valve of the implant and to initially form the valve, the source of test liquid (i.e., the syringe barrel 2) is raised vertically to a position such that the surface 20 of the test liquid 4 in the syringe barrel 2 is located approximately 54 cm above the location of the desired position of the implant valve. As illustratively shown in the drawings, this may be accomplished manually, or alternatively automated motorized means as discussed above may be used. The source S is thereafter maintained in this position, for example by attaching the source syringe to a vertical pole with an elastic band. It, of course, again will be understood that a more sophisticated source movement and retaining means may be utilized without departure from the invention.

The valve in the latter situation is then cut in the drainage tube. This is done under microscopic observation (magnification between about 6 and about 90 diameters, normally about 25 diameters) in air with oblique white light illumination. The valve is cut with an instrument such as the razor blade fragment knife shown in FIG. 3 in a single smooth motion so as to form a longitudinal slit in the drainage tube extending approximately 3 mm to 4 mm from the blocked tube end toward the open tube end. This method of forming the valve begins a flow of perfusing test liquid through the valve immediately. Hence, the valve is both wetted and forced open at the time of its initial formation. This facilitates the calibration of the implant during manufacturing thereby reducing quality assurance costs associated with testing implants at a time significantly removed from the time of valve formation. Again as alluded to above, this is because there is no necessity to either wet the leaflets of the valve, nor to manipluate the valve in order to overcome either surface tension effects or the valve's inertia against opening, at the time calibration testing is performed.

The implant is next mounted in a controlled fluid environment representatively shown as water bath W. As previously noted, this mounting of the implant is accomplished in a manner such that the valve may be readily microscopically observed yet retained in an environment which approximates that of the tissues in and surrounding the eye.

Thereafter, the source of test liquid, here syringe barrel 2, is moved vertically upwardly and downwardly while being shaken horizontally as discussed above. Moving the source upwardly increases the applied pressure on the implant valve and eventually causes the valve to open. At that point, a flow of test liquid through the valve may be detected and note taken of the pressure at which the valve opening occurred. Subsequently, the source is moved vertically downwardly while being shaken horizontally as discussed above. This downward motion of the source reduces the pressure applied to the valve until the valve closes. Such closure of the valve is detected by the observation and/or detection of the cessation of test liquid flow through the valve, and note is taken of the pressure at which the cessation of test liquid flow occurred. Typically, this opening and closing sequence of the valve of the implant being tested is repeated three (3) or more times in order to assure the repeatability of the test results.

Then the implant is tested for reflux (i.e., backflow) at reduced pressures relative to the pressure of valve closure. This is accomplished by moving the source of test liquid further downwardly while still shaking it horizontally to a location approximately 30 cm below the level at which test liquid flow through the valve ceased. This applies a pressure of about 20 mm Hg less than the valve closure pressure to the valve. Further, while this further downward movement of the source takes place, the valve and drainage tube are observed in order to determine whether or not liquid flows from the water bath W back into the drainage tube through the valve. If any such reflux is observed, the implant is destroyed as being unsatisfactory.

The purposes of a glaucoma drainage implant with a one-way, pressure gradient limiting valve include not only the drainage of aqueous humor from the eye, but also doing so in a manner which reduces the tendency toward overdrainage exhibited by unvalved tubes in such devices. This is due to the presence in the drainage pathway of a valve having a real opening and a real closing pressure in the wet environment of the orbit of the eye. Overdrainage is physiologically damaging in that it causes the anterior chamber of the eye to collapse inwardly upon itself, thereby adversely affecting vision and potentially permanently deforming the eye itself. A one-way, pressure gradient limiting valve allows the "bleb" to pressurize the liquid flow through the drainage tube at a level of pressure above the average pressure in the eye, if no backflow (reflux) can occur.

The foregoing raising and lowering of the source of test liquid is then repeated at least three (3) times over the course of the following fifteen minutes to one hour. The opening pressure of the valve and the closing pressure of the valve are noted in each case along with the presence or absence of any reflux. This provides a set of measurements which can be statistically analyzed so as to provide a reliable indication of the physiological operability of the implant which may be expected upon its implantation into the patient.

In the latter regard, it is to be understood that visualization of the valve is improved by moving clear liquid near the valve, for example by agitating the liquid of the water bath, or by squirting a clear watery solution over the valve site. Further, it is to be understood that with Joseph implants it has been determined that if opening and closing valve pressure measurements are repeatable again and again within a deviation of plus or minus 1 mm Hg within the 4–20 mm Hg pressure range, the implant may be considered as potentially worthy of clinical use.

Finally, the test method concludes by the formation of a hole in the explant band, for example with a 2 mm diameter steel trephine, at a predetermined location indicative of the opening pressure of the valve rounded off to the nearest mm Hg in the 4–20 mm Hg range. This hole allows the manufacturer, tester and/or surgeon to know both that the implant has been tested and that it has passed a calibration test meeting the indicated opening pressure value. Therefore, provided that care is taken to ensure that the valve is manipulated and flushed through prior to implantation as discussed above, it may be deemed worthy of further clinical experimentation either in vitro or in vivo.

Other test steps have also been found to be useful with the Joseph implant. Specifically, the explant in the Joseph device is a strip formed as a continuous strap around a mold portion. If the device is tested while on this mold portion, the continuous strap may be cut and trimmed subsequent to valve testing to size the strap and so as to remove any extraneous material which may be present.

Further, it has been found to be expedient to clean Joseph implants in batches in four (4) consecutive stainless steel pots. The first pot contains a boiling dilute, but foam containing, solution of pure soap such as sodium stearate in distilled water. The subsequent three (3) pots each contain boiling distilled water. The implants are placed in the soap solution for between about 30 minutes and about 60 minutes, and in each of the boiling water pots for between about 15 minutes and about 60 minutes. This procedure has been found to substantially clean the implants and to remove all significant traces of dye or other colorant or surfactant used in the test liquid from the internal surfaces if the implants so treated.

After cleaning, each of the wet implants are placed in a dry, chemically clean, container. Thereafter, they are dried in an environment of dry heat in a controlled heating apparatus for between about one (1) hour and about eight (8) hours. Subsequently, the containers are cooled to room temperature, closed and sealed. Sterilization is done by opening the packages, and autoclaving the contents prior to surgery. As a practical matter, it is envisioned that implant devices of the type discussed above will be randomly tested by the above method after sterilization to ensure that such sterilization has not undesirably altered the properties of the implant.

The implants so tested and packaged may be randomly retested if desired in the same manner as set forth above in the context of testing directly following manufacture. As indicated several times above, the only significant additional step required for such retesting is that the valve must be "flushed through" and have the valve leaflets manipulated and wetted prior to such retesting. This may be accomplished by mechanically separating the valve leaflets in a watery solution with a small blunt instrument. It also may be accomplished by the flow through procedure discussed in detail above (i.e., by "flushing through" the tube and valve of the device being tested with a tuberculin syringe or other source of fluid under substantial pressure). The important point is that the initial inertia of the valve leaflets to opening must be overcome by manipulation and the van der Waals forces between the smooth edges of the leaflets must be reduced by wetting.

Joseph devices which have undergone testing in the above manner have to date demonstrated valve opening and closing pressures in the 4–20 mm Hg range which remain substantially constant over time.

In addition, it is to be noted that the above described method does not suffer from the following disadvantages of prior methods of testing one-way, pressure gradient limiting glaucoma drainage devices.

1) The present test method allows no air/water surface tension to resist the initiation of flow from the valve as the applied pressure gradient is increased, nor does it encourage the cessation of flow though the valve as the applied pressure gradient is decreased as a result of the same surface tension phenomenon.

2) The present test method widely opens and thoroughly wets the valve surfaces before testing. This enables the tester to achieve relatively reproducible test results in comparison to test methods wherein the valves are opened either very slightly or not at all prior to testing.

3) The present test method's use of a fluctuating applied pressure superimposed on a gradually variable absolute pressure and testing under a liquid overcomes the inertia of the valve leaflets and allows a more consistently reproducible set of repeated consecutive measurements to be obtained than if pressure is applied which changes only gradually and smoothly with time. This gives the implant maker some level of confidence that the implant is physiologically relevant and useful.

4) The present method's use of fluctuating pressures and under liquid test environments allows for the discovery of new valve designs and their quality control which were not possible with prior testing methods.

5) The present method allows for the detection of reflux flow at moderately reduced pressure levels.

6) The present method, by the use of fluctuating applied pressure and under liquid test environments allows the discovery of glaucoma valve implant designs and their quality control which demonstrate fewer complications from overdrainage in the immediate postoperative period than unvalved Schocket tubes.

7) The present invention, by the use of fluctuating pressures and under liquid test environments allows the discovery of glaucoma valve implant designs and their quality control which exhibit better intra-ocular pressure control at one year than has heretofore been obtained with two-plate Molteno implants.

Various further modifications, alterations, variations and changes will occur to those skilled in the art in view of the foregoing detailed description of a presently preferred embodiment of the present invention.

For example, the air/liquid interface at the valve exit discussed above rather than being eliminated, might be altered in an important and practical way. Specifically, a suitable surfactant could be utilized to essentially eliminate the surface tension disparity at the valve exit during valve testing for opening and closing pressure. As used herein the term "suitable surfactant" means not only such preparations as a solution of a single type or members of a single class of surfactants, but also includes mixtures of agents belonging to at least two classes of surfactants, and mixtures including one or more of each of numerous surfactant classes as well as other ingredients. Hence, certain commercially available dishwashing detergents such as that sold under the tradename "Fairy Liquid" by Proctor and Gamble Limited in the United Kingdom and Northern Ireland which contain less than 5% amphoteric surfactants, 5–15% nonionic surfactants and 15–30% anionic surfactants are deemed to be satisfactory.

Thus, when a powerful surfactant such as 2 to 4 drops of the above-mentioned dishwashing liquid detergent or its equivalent were utilized per twenty (20) milliliters of water or saline solution to wet the abutting surfaces of a Joseph slit valved glaucoma drainage implant, it was found that the opening and closing pressures measured for the valve in air were substantially the same (to within the nearest mmHg) as when the same device was tested by the foregoing method in an under liquid environment. In addition, these results were reproducible over time in different test series.

Accordingly, it is contemplated that the above method might dispense with the under liquid environment in favor of testing in air despite the fact that the air environment is not even close to the wet tissue environment of the eye. This has the potential advantage of reducing test apparatus cost and complexity and thereby being more practical and efficient than the version of the present method described in detail hereinabove.

Other potential advantages of such a modification of the preferred method of this invention are as follows:

1) It would be possible to use non-manual means to propel the liquid and to record parameters such as temperature, valve opening and closing and applied mean pressure gradients and flow rates (including flow rates at various dynamic average pressure gradients over extended time periods).

2) It would be possible to more efficiently cause and record a large number of valve openings and closings with the pressures associated with each over extended periods of time than in an under liquid environment. This means that accelerated fatigue testing of one-way, pressure gradient limiting valves in glaucoma drainage implants could be conducted at less cost, with greater automation, and with improved accuracy than when such testing is conducted in an under liquid environment.

3) It would be more cost efficient to be able to test batches of implants, rather than individual implants in a non-liquid environment. This could lead to the discovery of improved materials and designs for glaucoma drainage implant devices which might otherwise not be pursued in view of their cost and the complexity, and time required for under liquid testing.

In each of the latter cases, however, it must be clearly understood that the modification of the present method to an "in air" method, rather than an under liquid method, requires the surfactant work over extended periods to wet the valve leaflets in a manner at least equivalent to the wetting provided by the under liquid environment. Cost advantages are envisioned for the "in air" method over the under liquid method, but those advantages must be balanced against the removal of the test apparatus from an approximation of the environment of the wet tissue of the eye.

Present results with surfactants suggest that such a change in environment is not critical so long as adequate valve leaflet wetting is maintained. It is not clear, however, whether or not the under liquid environment described herein may otherwise be of significant import in the determination in vitro of the suitability of a particular implant for in vivo usage.

It will, of course, be understood that all of the above test measurements are achievable in an under liquid environment, and that this may be found to be preferable, especially as a reference standard.

I, therefore, claim:

1. A method for in vitro testing one-way pressure gradient limiting valved glaucoma drainage implants having drainage tubes, said method comprising the steps of:
   a. providing:
      i) source means for providing a flow of test liquid;
      ii) first pressure application means for applying an absolute pressure gradient across the valve being tested;
      iii) means for measuring the absolute pressure gradient applied to the valve;
      iv) second pressure application means for superimposing a fluctuation on the applied absolute pressure gradient;
      v) recording means for recording valve opening and valve closing pressures;
      vii) first flow detection means for determining the presence and/or absence of flow from the valve output;
      viii) a fluid environment;
      ix) support means in the fluid environment for holding at least the valve portion of the implant to be tested;
      x) second flow detection means for determining the quantity of flow through the valve output;
      xi) connection means for conveying test liquid from the source to the free end of the drainage tube of the implant; and
      xii) means for manipulating the valve being tested;
   b. manipulating the valve to be tested with the manipulating means;
   c. mounting at least the valved portion of the implant on the support means in the fluid environment;
   d. connecting the free end of the drainage tube of the implant to the source via the connecting means;
   e. applying the testing liquid to the valve under the influence of said first and second pressure application means;
   f. gradually increasing the absolute applied pressure until test liquid flow through the valve is detected by said first fluid flow detection means and recording that absolute pressure value;
   g. gradually reducing the absolute applied pressure until test fluid no longer is detected by said first fluid detection means and recording that absolute pressure value;
   h. determining by said second fluid flow detection means and recording the quantity of test fluid which passed through the valve between steps (e) and (g); and
   i. reducing the absolute pressure to a level about 20 mm Hg below the pressure at which liquid flow through the valve ceased so as to ensure the absence of backflow through the valve.

2. The method according to claim 1 further comprising the step of inspecting the one-way, pressure gradient limiting valved glaucoma drainage implant to be tested for defects prior to step (b).

3. The method according to claim 1 wherein the apparatus provided in step (a) further comprises timing means for determining elapsed test time.

4. The method according to claim 1 wherein the apparatus provided in step (a) further comprises heat control means for controlling the ambient temperature of the test site.

5. The method according to claim 1 wherein said fluid environment comprises a liquid bath.

6. The method according to claim 1 wherein said fluid environment is gaseous and said valve is wetted with a surfactant material.

7. The method of claim 1 wherein said test liquid is selected from the group consisting of water, a saline solution, and liquid materials having properties similar to those of aqueous humor.

8. The method of claim 7 wherein said test liquid includes a component adapted to color the test fluid so as to facilitate the detection of the initiation and cessation of test fluid flow through said valve.

9. The method of claim 8 wherein the apparatus provided in step (a) further comprises illumination means adapted to facilitate the visual detection of the initiation and cessation of test liquid flow through said valve.

10. The method according to claim 1 wherein said manipulation means comprises a device for mechanically opening said valve.

11. The method according to claim 1 wherein said manipulation means comprises a flow of liquid at high pressure applied to said valve so as to assure the mechanical opening of said valve prior to the testing thereof.

12. The method according to claim 11 wherein said fluid environment comprises a liquid.

13. The method according to claim 11 wherein said fluid environment is gaseous in nature, wherein said manipulation means comprises a flow of liquid containing a surfactant composition, and said liquid is applied to said valve at high pressure so as to assure the mechanical opening of said valve and the wetting of said valve with said surfactant composition.

14. The method according to claim 1 further comprising the provision of cutting means, and the step of enlarging said valve of said implant with said cutting means when said measured valve opening pressure is greater than a preselected desired value.

15. The method according to claim 1 further comprising the provision of a microscopic viewing device having a preselected field of view and a preselected magnification range, and the accomplishment of at least steps (f), (g) and (i) while said valve is located within said field of view of said microscopic viewing device.

16. The method according to claim 1 wherein said first pressure application means comprises an open topped reservoir of test fluid having an upper surface, said upper surface being vertically moveable between a first preselected height above the location of the valve of the implant being tested and and a second preselected height below the location of the valve of the implant being tested.

17. The method according to claim 1 wherein said first pressure application means comprises a motorized syringe.

18. The method according to claim 16 wherein said second pressure application means is adapted to substantially horizontally vibrate said reservoir so as to cause pressure fluctuations superimposed upon the pressure applied to said test fluid by said first pressure application means.

19. The method according to claim 17 wherein said vibration is applied to said reservoir at a physiologically relevant amplitude and frequency.

20. The method according to claim 17 wherein a motorized element is located in mechanically coupled relation to said reservoir, and said motorized element applies its natural vibratory motion to said reservoir through said coupling.

21. The method according to claim 19 wherein said motorized element includes controls adapted to vary the natural vibratory motion of said motorized element within a preselected range.

22. The method according to claim 1 wherein the test liquid is applied to the valve of the implant being tested by gravity feed.

23. The method according to claim 1 wherein the test liquid is applied to the valve under a mechanically generated absolute pressure.

24. The method according to claim 1 wherein said recording steps are accomplished by a strip recorder coupled to a manometer.

25. The method according to claim 24 wherein said manometer is selected from the group consisting of mechanical and electrical sensors disposed within said connecting means, microscopic instruments and photo-optic devices.

26. The method according to claim 25 wherein said microscopic devices comprise dissecting microscopes having magnification ranges between about 6 diameters and about 90 diameters.

27. The method according to claim 25 wherein said photo-optic devices comprise at least one light beam source and at least one photodetector, said light beam source being adapted to direct a light beam from one side of the valve being tested across the valve opening, and the photodetector being located on the opposite side of said valve opening and adapted to generate a signal in response to interruptions in said light beam for transmission to said recording means.

28. The method of claim 1 wherein said means for superimposing a fluctuation upon said absolute applied pressure gradient comprises means coupled to said test fluid source and/or said connecting means selected from the group consisting of a variable speed electrical air pump, a motorized vibrator, and an AC driven electromagnet including an associated movable ferromagnetic element.

29. The method according to claim 1 wherein said connecting means is at least partially disposed between the contacts of an electromagnetic device adapted to periodically exert a compressive force on the connecting means in response to an applied alternating current whereby fluctuations are superimposed upon the absolute pressure of the test fluid flowing through said connecting means.

* * * * *